United States Patent
Schmidt et al.

(10) Patent No.: US 6,416,951 B1
(45) Date of Patent: Jul. 9, 2002

(54) SCREENING FOR FUNCTIONAL ANTISENSE AGENTS

(75) Inventors: Gunter Schmidt, Cambridge; Andrew Hugin Thompson, Avr, both of (GB)

(73) Assignee: Brax Group Ltd., Cambridge (GB)

( * ) Notice: Subject to any disclaimer, the term of this patent is extended or adjusted under 35 U.S.C. 154(b) by 0 days.

(21) Appl. No.: 09/623,385

(22) PCT Filed: Mar. 3, 1999

(86) PCT No.: PCT/GB99/00631

§ 371 (c)(1),
(2), (4) Date: Mar. 26, 2001

(87) PCT Pub. No.: WO99/45145

PCT Pub. Date: Sep. 10, 1999

(30) Foreign Application Priority Data

Mar. 3, 1998 (GB) ............................................. 9804526

(51) Int. Cl.$^7$ ................................................. C12Q 1/68
(52) U.S. Cl. ........................................................... 435/6
(58) Field of Search ............................................ 435/6

(56) References Cited

U.S. PATENT DOCUMENTS 5,750,337 A * 5/1998 Squirrell ........................ 435/6

FOREIGN PATENT DOCUMENTS

| WO | WO-95/21265 | * | 8/1995 |
| WO | WO97/27331 |   | 7/1997 |
| WO | WO98/15651 |   | 4/1998 |

OTHER PUBLICATIONS

Yguerabide, J. et al., "Quantitative Fluorescence Method for Continuous Measurement of DNA Hybridization Kinetics Using a Fluorescent Intercalator", Anal. Biochem. vol. 228, pp. 208–220 (1995).*

Stimpson, D.I. et al., "Real–time detection of DNA hybridization and melting on oligonucleotide arrays by using optical wave guides", PNAS USA, vol. 92, pp. 6379–6383 (1995).*

Stimpson, Don et al., "Real–time detection of DNA hybridization and melting on oligonucleotide arrays by using optical wave guides" *Proc. Natl. Acad. Sci. USA,* vol. 92, (Jul. 1995) pp. 6379–6383.

Schwille, Petra et al., "Quantitative Hybridization Kinetics of DNA Probes to RNA in Solution Followed by Diffusional Fluorescence Correlation Analysis" *Biochemistry,* vol. 35 (1996) pp. 10182–10193.

Ishiguro, Takahiko et al., "Fluorescence detection of specific sequence of nucleic acids by oxazole yellow–linked oligonucleotides. Homogeneous quantitative monitoring of in vitro transcription" *Nucleic Acids Research,* vol. 24, No. 24 (1996) pp. 4992–4997.

Abstract—Yguerabide, J. et al., "Quantitative fluorescence method for continuous measurement of DNA hybridization kinetics using a fluorescent intercalator",*Analytical Biochemistry,* vol. 228, No. 2, (Jul. 1995) pp. 208–220.

Abel, Andreas et al., "Fiber–Optic Evanescent Wave Biosensor for the Detection of Oligonucleotides" *Anal. Chem.,* vol. 68 (1996) pp. 2905–2912.

Bier, Frank F. et al., "Real–time measurement of nucleic–acid hybridization using evanescent–wave sensors: steps towards the genosensor" *Sensors and Actuators B.* 38–39 (1997) pp. 78–82.

* cited by examiner

*Primary Examiner*—Kenneth R. Horlick
*Assistant Examiner*—Teresa Strzelecka
(74) *Attorney, Agent, or Firm*—Robin L. Teskin

(57) ABSTRACT

Provided is a method for identifying a functional antisense agent, which method comprises hybridizing an RNA with an aligonucleotide probe and measuring in real time the kinetics of hybridization, wherein the kinetics are measured by either hybridizing in the presence of an intercalation dye and recording a change in the spectroscopic properties of the dye as hybridizing proceeds, or incorporating a label in either the RNA or the probe, attaching the non-labelled RNA or non-labelled probe to a solid support, generating an evanescent wave in the proximity of the non-labelled RNA or non-labelled probe and recording the increase in a signal generated by interaction of the evanescent wave with the label, as hybridization proceeds.

20 Claims, No Drawings

SCREENING FOR FUNCTIONAL ANTISENSE AGENTS

The present application concerns methods for the identification of functional antisense agents. In particular, the present application is concerned with improved methods for measuring the kinetics of the hybridisation of RNA and antisense oligonucleotides.

WO 98/15651 provides methods to identify regions in the primary sequence of a target RNA that are accessible to hybridisation probes. The methods involve hybridising short oligonucleotide probes to the target RNA in separate reaction zones. The sequences of the hybridising probes are compared with the primary sequence of the target RNA to identify probes which hybridise to overlapping sequences in the target RNA. These sequences identify accessible regions in the target RNA. WO 98/15651 further describes the use of radiolabelling as an embodiment of the invention in which the hybridisation reactions between the probes of that invention and a target RNA can be followed in real time.

It is an object of this invention to provide non-radioactive methods for following the hybridisation reactions described in WO 98/15651 in real time. It is also object of this invention to provide compounds and kits to practice the methods of WO 98/15651. The methods of RNA analysis described in this prior patent application are based on hybridising an array of oligonucleotides to a target RNA. In the earlier application the hybridisation reactions between each member of the array and the target RNA are performed in spatially separated reaction vessels. It is a further object of this invention to provide methods of analysing a target RNA that generate the same data as the methods of the previous disclosure without requiring complete spatial separation of all of the probes in the array used to analyse the target RNA.

Accordingly, the present invention provides a method for identifying a functional antisense agent, which method comprises hybridising an RNA with an oligonucleotide probe and measuring in real time the kinetics of hybridisation, wherein the kinetics are measured by either hybridising in the presence of an intercalation dye and recording a change in the spectroscopic properties of the dye as hybridising proceeds, or incorporating a label in either the RNA or the probe, attaching the non-labelled RNA or non-labelled probe to a solid support, generating an evanescent wave in the proximity of the non-labelled RNA or non-labelled probe and recording the increase in a signal generated by interaction of the evanescent wave with the label, as hybridisation proceeds, and wherein the oligonucleotide probe comprises an array of oligonucleotides, each oligonucleotide in the array having a common length of 4 to 8 nucleotides, all possible base sequences of that length being represented in the array.

This invention also provides a kit for identifying a functional antisense agent, comprising an oligonucleotide probe, and a means for generating a signal for measuring the kinetics of hybridisation of the oligonucleotide probe to an RNA, wherein the oligonucleotide probe comprises an array of oligonucleotides, each oligonucleotide in the array having a common length of 4 to 8 nucleotides, all possible base sequences of that length being represented in the array.

Detection using evanescent waves

A non-radioactive method to determine the kinetics of hybridisation reactions of the sort described in WO 98/15651 in real time would be preferable to radiolabelling for safety reasons. A method of measuring the kinetics of nucleic acid hybridisation is described by D. I. Stimpson et al in Proc. Natl. Acad. Sci. USA, 92: 6379–6383, 1995. The method disclosed in this publication measures the hybridisation of a labelled oligonucleotide probe to a target immobilised at the surface of a two dimensional optical wave guide. An optical wave guide that is transmitting light generates an>evanescent wave×which extends some distance above the surface of the wave guide. Light from the evanescent wave can be scattered by a particulate label near the surface of the wave guide. This scattered light can be detected by a Charge Coupled Device camera, a fluorescent microscope or any other appropriate optoelectronic detection instrument. The quantity of scattered light is a measure of the quantity of particulate label near the surface of the wave guide. The evanescent wave extends only about 100 to 300 nm beyond the surface of the wave guide so only labelled material close to the surface of the wave guide will scatter light. This is ideal for measuring binding, unbinding or cleavage events close to the surface of the wave guide as a binding reaction at the surface of the wave guide will greatly increase the quantity of labelled probe within the evanescent wave over the background of label present free in solution. If a target RNA molecule is labelled with an appropriate particulate label the methods of the above publication could be applied with the methods of this invention. In the above publication by Stimpson et al, 200 nm selenium particles were conjugated with an anti-biotin antibody and linked to biotinylated oligonucleotide probes. Biotinylation of one terminus of a target RNA would allow a similar label to be used with this invention.

An embodiment of this invention using fluorescently labelled RNA may comprise the following steps:

1. Generating target RNA labelled with biotin.
2. Reacting the labelled RNA with a selenium/avidin conjugate to label the RNA with a light scattering particle of selenium.
3. Hybridising the labelled RNA to an array of the oligonucleotide probes of this invention. Such an array can be synthesised on the surface of a 2 dimensional wave guide as discussed briefly below.
4. Recording in real time the increase in light scattered by the labelled RNA from each field of the oligonucleotide array. Over the time course of the hybridisation reaction between the labelled target RNA and the oligonucleotide probe at a particular position on the array, the quantity of light scattered from the surface of the optical wave guide increases if the labelled RNA hybridises to the probe. The rate at which the light scattering from the surface of the wave guide increases is a measure of the rate of the hybridisation reaction occurring and is indirectly a measure of the accessibility of the binding sites in the RNA complementary to the probe at a given point on the oligonucleotide array. One would expect there to be a background count from labelled RNA fragments free in solution close enough to the wave guide surface to be detected, so control reactions must be performed with labelled RNA free in solution.
5. Comparing the primary sequence of the target RNA with the sequences of the probes that hybridise with the fastest kinetics to identify regions of the target RNA which are accessible to oligonucleotide probes.

Accessible regions in a target RNA are expected to hybridise to probes with overlapping sequences. It is thus assumed that probes with overlapping sequences that hybridise to a target RNA are hybridising to an accessible region in the RNA. The kinetics of these binding reactions can give additional information as can the use of 2° structure models for an RNA target.

It is an objective of this invention to identify sites in an RNA that have a preferred minimum of at least 7 bases of contiguous accessible sequence.

Similarly, in an alternative embodiment, the target RNA can be immobilised on a solid phase substrate in distinct reaction zones and individual labelled probes can be hybridised to the target RNA. A different probe is added to each reaction zone. If, for example, 256 4-mer probes are used, the target RNA is immobilised in 256 distinct wells on a micro-plate and one labelled probe of the array is hybridised with the RNA in each well.

Oligonucleotide Arrays

Arrays of oligonucleotides are a relatively novel approach to nucleic acid analysis, allowing mutation analysis, sequencing by hybridisation and mRNA expression analysis. Methods of fabricating such arrays have been developed, (see for example: A. C. Pease et al. Proc. Natl. Acad. Sci. USA 91, 5022–5026, 1994; U. Maskos and E. M. Southern, Nucleic Acids Research 21, 2269–2270, 1993; E. M. Southern et al, Nucleic Acids Research 22, 1368–1373, 1994) and further methods are envisaged.

Evanescent Wave Fluorescence

The evanescent wave of an optical wave guide can also excite fluorescence emission from fluorescent dyes near the surface of the wave guide (I. Gryczynski et al., Anal. Biochem. 247, 69–76, 1997 and A. P. Abel et al., Anal. Chem. 68, 2905–2912, 1996). Fluorescence emissions of this sort can also be detected by a Charge Coupled Device camera or using other optoelectronic detection systems. The quantity of fluorescence emitted is a measure of the quantity of fluorescent label near the surface of the wave guide. The principal is essentially similar to that described above for evanescent wave scattering. If a target RNA molecule is labelled with an appropriate fluorescent dye the methods of the above publication can be applied in the methods of this invention.

An embodiment of this invention using fluorescently labelled RNA may comprise the following steps:

1. Generating a fluorescently labelled target RNA.
2. Hybridising the fluorescently labelled RNA to an array of the oligonucleotide probes of this invention. Such an array can be synthesised on the surface of a 2 dimensional wave guide as discussed above.
3. Recording, in real time, the increase in fluorescent signal from the labelled RNA from each field of the oligonucleotide array. Over the time course of the hybridisation reaction between the labelled target RNA and the oligonucleotide probe at a particular position on the array, the quantity of fluorescence emitted from the surface of the wave-guide increases if the labelled RNA hybridises to the probe. The rate at which the fluorescence from the surface of the wave guide increases is a measure of the rate of the hybridisation reaction occurring and is indirectly a measure of the accessibility of the binding sites in the RNA complementary to the probe at a given point on the oligonucleotide array. One would expect there to be a background count, from labelled RNA fragments free in solution close enough to the wave guide surface to be detected, so control reactions must be performed with labelled RNA free in solution.
4. Comparing the primary sequence of the target RNA with the sequence of the probes that hybridise with the fastest kinetics to identify regions of the target RNA which are accessible to oligonucleotide probes.

Similarly the target RNA can be immobilised on a solid phase substrate in distinct reaction zones and individual fluorescently labelled probes can be hybridised to the target RNA. A different probe is added to each reaction zone. If, for example, 256 4-mer probes are used, that target RNA is immobilised in 256 distinct wells on a micro-plate and one labelled probe of the array is hybridised with the RNA in each well.

Intercalating Dyes

A further non-radioactive method of measuring the kinetics of hybridisation of the probes of this invention in real time involves the use of intercalating dyes. These are compounds that can intercalate between the stacked planes formed when nucleobases hybridise correctly in a nucleic acid duplex. The spaces between stacked bases provide a hydrophobic environment. Intercalating dyes are fluorescent markers whose fluorescence is quenched in a polar environment, i.e. when the dye is in an aqueous solution, but in a hydrophobic environment fluorescence is detectable. Intercalation is accompanied by a change in some property of the molecule detectable by optical spectrometry such as a shift in the fluorescence emission frequency of the molecule.

The types of dye usable in the present invention are not especially limited, however, a typical useful intercalating dye is ethidium bromide which can be linked to an oligonucleotide probe in a variety of positions with an alkyl linker. Yguerabide et al., Anal. Biochem. 228: 208–220, 1995 describes a method for continuous measurement of DNA or RNA hybridisation using ethidium bromide. An oligonucleotide probe carrying a covalently linked intercalating dye is detectable by fluorescence only when hybridised with RNA to form a duplex. There is, at least, a marked increase in fluorescence on hybridisation. Thus the kinetics of a hybridisation reaction between an oligonucleotide probe and its target can be followed by monitoring changes in fluorescence emissions from the reaction vessel. Other dyes besides ethidium bromide are known which have more marked increases in fluorescence on binding to a DNA duplex over the fluorescence of the dye free in solution. Examples of such dyes which can also be used in the present invention include thiazole orange and oxazole yellow and the respective homodimers of these compounds. (see Nature 359, 859–861). Ishiguro et al., Nucleic Acids Research 24: 4992–4997, 1996 describes the use of oxazole yellow-linked oligonucleotides to monitor hybridisation to a target RNA as it is transcribed.

The binding activity of probes bearing intercalating dyes can be monitored using a variety of optical detection techniques including confocal fluorescent microscopy or using evanescent wave fluorescence as discussed above. (P. C. Pandey et al., Appl. Biochem. Biotechnol. 55, 87–92, 1995).

Schwille et al., Biochem. 35: 10182–10193, 1996 describes an alternative method of monitoring hybridisation of DNA probes to RNA by diffusional fluorescence correlation analysis. In this study 6 specific probes complementary to a particular target RNA were used to assess the method, which uses changes in translational diffusion time to measure hybridisation of a fluorescent probe to a target RNA.

Addition of probes to target RNA

Patent application WO 98/15651 provides methods to identify which regions in the primary sequence of a target RNA molecule are accessible to hybridisation probes. The method measures the hybridisation of a family of nucleic acid probes of a fixed length. The hybridisation of these oligonucleotides (ONs) is tested individually in the method disclosed in WO 98/15651. In one embodiment of the invention disclosed in WO 98/15651 the target RNA is immobilised and the RNA is challenged with individual, labelled ONs. In an alternative embodiment the probes are immobilised and the immobilised probes are challenged with the target RNA. Thus for a library of ONs of 4 nucleotides, an array of 256 wells is required, in each of which equal quantities of RNA are immobilised or in each of which a unique probe is immobilised. Each well is challenged with a different labelled ON in the former case or labelled target RNA in the latter. The probe oligonucleotide and RNA are allowed to hybridise for a predetermined length of time and the unhybridised ONs are then washed off. The quantity of On hybridised is determined by measuring the label retained in each well.

Complete isolation of probes from each other as disclosed in WO 98/15651 is not necessary in this invention. Thus, this invention provides a method in which probe do not need to be added individually to a target RNA.

Non-overlapping probe sets

In WO 98/15651, the oligonucleotide probes of that invention are labelled with a single reporter group since the probes are analysed independently of each other. However if more then one uniquely resolvable reporter groups are available, more probes can be hybridised to a target RNA molecule simultaneously. With four fluorescent dyes, one can add four 'non-overlapping' probes to each sample of immobilised RNA simultaneously. Non-overlapping in this context means that the probes do not share any subsequence so that they would be guaranteed not to compete for overlapping sites in a target RNA. With more labels, one can quite easily add more probes simultaneously, preferably as 'non-overlapping sets'. A labelling system which permits the construction of large numbers of labelled hybridisation probes is described in patent application WO 98/31830, which describes the use of mass labels. Mass labels are small molecule compounds, preferably less than 2 kilodaltons in mass, that have desirable properties for detection in a mass spectrometer, as discussed in the above patent application. These labels are cleavably linked to oligonucleotide probes allowing them to be removed in a controllable manner for analysis by mass spectrometry.

Table 1 lists 64 sets of 4 non-overlapping and non-complementary 4-mer oligonucleotides which can be labelled with 4 fluorescent dyes with distinct emission characteristics. Sets of this form can be identified relatively easily using simple sequence comparison algorithms to decide whether groups of oligonucleotide probes overlap or whether they are complementary. This requires only 64 distinct hybridisation reactions to be carried out for each target RNA, where 4 probes are incubated with the target RNA in each reaction and the hybridisation of each is determined by measuring fluorescence at each four distinct emission frequencies. The hybridisation of such fluorescently labelled probes can be monitored using evanescent wave fluorescence as discussed above.

In one embodiment, if cleavable mass labels are used, all 256 probes can be labelled with a distinct mass label. The 256 mass labelled probe sets are incubated with the target RNA in 64 distinct reaction vessels. After a predetermined period, unhybridised probe is washed away and the labels on the hybridised probe are analysed by mass spectrometry. The labels are cleaved in the reaction vessel and delivered to the mass spec, or the hybridised probes from each reaction vessel are solvated and pooled and the labelled probes are fed directly into a mass spectrometer according to the methods of WO 98/31830 where the labels are cleaved within the mass spectrometer before analysis.

TABLE 1 list of non-overlapping and non-complementary 4-mers

| | | | |
|---|---|---|---|
| aaaa, caac, | aaca, ccac, | gagt, gatt, | gcgt, gctt, |
| gaag, taat | gaat, gact | gcat, gcct | gggt, ccct |
| aacc, aacg, | aagg, aagt, | aatt, acac, | acaa, cacc, |
| aact, aagc | aatc, aatg | agag, atat | gacg, tact |
| cagg, cagt, | ccgg, ccgt, | cgag, cgat, | acag, acat, |
| catg, catt | cctg, cctt | cgct, gtgt | accc, accg |
| acct, acgc, | actc, actg, | acca, cccc, | acga, cagc, |
| acgg, acgt | actt, cgtt | gagg, tagt | ggag, tatt |
| acta, catc, | agaa, ccgc, | agac, agat, | agct, aggc, |
| gcag, tgat | gatg, tcat | agcc, agcg | aggg, aggt |
| atta, cctc, | agga, cgac, | agta, cgcc, | ataa, cgcg, |
| gccg, tggt | gcgg, tcgt | gctg, tcct | ctag, ctgg |
| ctgt, cttg, | atac, atag, | atct, atgc, | atca, cggc, |
| cttt, cccg | atcc, atcg | atgg, atgt | gggg, tctt |
| atga, cggg, | caaa, caga, | ccta, cgga, | ctta, gcga, |
| cggt, cgtg | cata, ccga | cgta, ctga | gcta, ggga |
| ggta, gtga, | ccaa, cgaa, | ctat, gaga, | ccca, cgca, |
| gtta, gttt | ctaa, ttgt | gcaa, ggaa | ctca, gaaa |
| gaca, gata, | gtca, tcca, | tgta, ttaa, | ctac, ggcg, |
| gcca, ggca | tcta, tgca | ttca, ttgc | taaa, taga |
| tcaa, tcga, | ctcc, ggtg, | ctcg, taag, | tatg, tcag, |
| tgaa, tgga | taca, ttga | tacg, tagg | tctg, tttg |
| gaac, gacc, | ggcc, gtac, | gcac, gccc, | ggtc, gttc, |
| gagc, gatc | gtcc, tgct | gctc, ttct | taac, tacc |
| tatc, tgac, | gcgc, tcac, | gggc, tagc, | tcc, gtgg, |
| tgtc, tttc | tccc, tgcc | tcgc, tggc | tctc, ttta |
| tcgg, tgag, | agtc, agtg, | attc, attg, | aaag, caat, |
| tgcg, tggg | agtt, aaat | attt, aaac | cacg, cact |
| cttc, gtcg, | ttag, tgtg, | ggat, gtaa, | ctgc, gtag, |
| tgtt, aaga | tata, ttac | gtat, gtgc | tttt, aata |
| caag, ccag, | agca, cgtc, | ggct, ggtt, | ttcg, ttgg, |
| ccat, ctct | gttg, ttat | ggac, gtct | tccg, caca |

Competitive assays

Although a number of oligonucleotide probes in an oligonucleotide library might have overlapping sequences, there is only a small possibility that their target sequences will also overlap in the primary sequence of a target RNA, so if all 256 probes in a 4-mer library are hybridised simultaneously with a target RNA, it is likely that the majority of hybridisation reactions should not compete significantly with each other for binding sites in a target RNA. If all 256 probes in a library of 4-mers is hybridised to a target RNA simultaneously, however, there can be problems with cross hybridisation of probes in the library so labelled probes are preferably added in 2 complementary sets of 128 or as 4 sets of 64 of non-complementary probes. Competitive binding of oligonucleotide probes that have overlapping binding sites in the target mRNA can be used to identify sets in the tertiary structure of the RNA that are most accessible to oligonucleotides using far fewer hybridisation reactions, since 2 or 4 distinct reactions are sufficient. Such an approach is a quicker and cheaper way of determining the accessibility of sites in a target RNA than methods requiring complete spatial resolution of the arrays of probe oligonucleotides. Without complete spatial resolution of an array of oligonucleotide probes, one might expect a certain number of probes to compete for binding sites in a target RNA. With the primary sequence of the target RNA it is easy to determine which oligonucleotides in an array are going to compete for binding sits. Any competing probes can be resolved by repeating the hybridisation reactions of competing probes with spatially resolved probes, testing only those probes which compete.

Competitive assays are likely to be of great importance in identifying effective antisense agents as, ideally, those oligonucleotides that bind most readily are likely to be more effective antisense agents so identifying the most accessible regions in a molecule would be extremely valuable. An embodiment of a competitive binding assay according to this invention comprises the following steps:

1. Generating immobilised target RNA on a solid phase substrate.
2. Hybridising an array of oligonucleotides, where each unique oligonucleotide in the competitive assay is identified by a unique cleavable mass label.
3. Determining the quantity of oligonucleotide that has hybridised in each well after a predetermined period of time by washing away unhybridised probe and buffers and measuring how much of each hybridised probe remains associated with the immobilised RNA. The relative proportions of each label will reveal which oligos have hybridised most effectively in the time allowed.

These steps 1 to 3 may be repeated with the washing step being performed after varying incubation times to determine a time course for the cleavage reaction.

4. Comparing the primary sequence of the target RNA with the sequences of the probes that hybridise with the fastest kinetics to identify regions of the target RNA which are accessible to hybridisation probes.

Mass Spectrometry Analysis of Mass Labelled Hybridisation Probes

In the embodiment of this invention described above, identification of the oligonucleotide probes that remain hybridised to the immobilised RNA is performed using mass spectrometry. A number of mass spectrometry techniques can be exploited to analyse mass labelled hybridisaiton probes.

Matrix Assisted Laser Desorption Ionisation (MALDI) is a technique for ionising large organic molecules using laser excitation. Usually it is necessary to embed the analyte in a large molar excess of a photo-excitable 'matrix'. The application of laser light of the appropriate frequency (266 nm beam for nicotinic acid) results in the excitation of the matrix which in turn leads to excitation and ionisation of the embedded biomolecule. The detection of mass labelled oligonucleotide probes by MALDI techniques can be effected in two ways. In the first approach, the RNA/probe complexes are embedded into an excitable matrix, such as 3-hydroxypicolinic acid, after washing away any unhybridised probe. Application of laser light is used to desorb probes from the surface on which the hybridisation reactions were performed. In an alternative approach, the mass labels themselves are constructed so that they contain the necessary groups to allow laser energisation. The latter approach means the labels do not need to be embedded in a matrix before performing mass spectrometry. Typical laser excitable groups include nicotinic, sinapinic or cinnamic acid moieties. Cleavage of the mass labels from their probes can be readily effected during MALDI if a photocleavable linker is used to couple each mass label to its corresponding oligonucleotide probe, as this avoids a cleavage step prior to performing MALDI mass spectrometry. The various excitable ionisation agents have different excitation frequencies so that a different frequency can be chosen to trigger ionisation from that used to cleave the photocleavable linker. These excitable moieties are easily derivitised using standard synthetic techniques in organic chemistry so labels with multiple masses can be constructed in a combinatorial manner. Typically laser desorbed ions are then analysed in a Time Of Flight mass analyser.

Electrospray based mass spectrometry techniques are equally compatible with the embodiments of this invention that exploit mass labels. In step 3 of the embodiment described above, unhybridised probes are washed away and the labelled oligonucleotide probes that have hybridised to an immobilised target RNA are analysed. An electrospray analysis requires the hybridised probes to be denatured from the target RNA and released into an appropriate buffer which can then be injected into an electrospray source where ionisation and cleavage of mass labels from their probes occurs. Analysis of the cleaved labels is performed by the mass analyser coupled to the electrospray ion source. Numerous mass analyser geometries are routinely used with electrospray ionisation. These processes are discussed fully in WO 98/31830.

What is claimed is:

1. A method for identifying a functional antisense agent, which method comprises hybridising an RNA with an oligonucleotide probe and measuring in real time the kinetics of hybridisation, wherein the kinetics are measured by either:

(a) hybridising in the presence of an intercalation dye and recording a change in the spectroscopic properties of the dye as hybridising proceeds; or
   (b) labelling either the target RNA or the oligonucleotide probe, but not both and attaching the non-labelled entity to a solid support, generating an evanescent wave in the proximity of the non-labelled entity and recording the increase in a signal resulting from the interaction of the evanescent wave with the label as the labelled entity hybridises with the non-labelled entity;

and wherein the oligonucleotide probe conprises an array of oligonucleotides, each oligonucleotide in the array having a common length of 4–8 nucleotides, all possible base sequences of that length being represented in the array, said method further comprising comparing the primary sequence of the target RNA with the sequences of the probes that hybridise with the fastest kinetics to identify regions of the target RNA which are accessible to oligonucleotide probes.

2. A method according to claim 1, wherein the intercalation dye is ethidium bromide, thiazole orange or oxazole yellow.

3. A method according to claim 1, wherein the spectroscopic properties of the intercalation dye are measured using confocal fluorescent microscopy or evanescent wave fluorescence.

4. A method according to claim 1, wherein the label is a particulate label and the signal is scattering of the evanescent wave by the particulate label.

5. A method according to claim 4, wherein the particulate label comprises gold or selenium.

6. A method according to claim 1, wherein the label is a fluorescent label and the signal is fluorescence of the label generated by interaction of the label with the evanescent wave.

7. A method according to claim 1, wherein the solid support is a waveguide for producing an evanescent wave.

8. A method according to claim 4, wherein the scattering is measured using a fluorescence microscope.

9. A method according to claim 1, wherein the array is an array of 4-mers.

10. A method according to claim 1, wherein the oligonucleotide probe comprises multiple arrays of 4-mers.

11. A method according to claim 10, wherein the RNA is contacted with 64 arrays in 64 separate reactions, each array being comprised of 4 labelled 4-mers, each of the 4-mers in any one array being non-complementary to one another and non-overlapping with one another, and each of the 4-mers in any one array not being common to any of the other arrays and having a unique label.

12. A kit for identifying a functional antisense agent, which comprises:
   (a) an oligonucleotide probe comprising an array of oligonucleotides, each oligonucleotide in the array having a common length of 4–8 nucleotides and all possible base sequences of that length being represented in the array;
   (b) a means for generating a signal for measuring the kinetics of hybridisation of the oligonucleotide probe to an RNA; and
   (c) a means for comparing the primary sequence of the RNA with the sequences of the probes that hybridise with the fastest kinetics.

13. A kit according to claim 12, wherein the means for generating a signal comprises an intercalation dye.

14. A kit according to claim 13, wherein the intercalation dye is ethidium bromide, thiazole orange or oxazole yellow.

15. A kit according to claim 12, wherein the means for generating a signal comprises an optical waveguide for producing an evanescent wave.

16. A kit according to claim 12, wherein the array is an array of 4-mers.

17. A kit according to claim 12, wherein the oligonucleotide probe comprises a first array of 128 non-spatially separated labelled 4-mers and a second array of 128 non-spatially separated, labelled 4-mers, wherein each of the 4-mers in the first array is different from one another and non-complementary to one another, and each of the 4-mers in the second array is different from one another, each of the 4-mers in the first array being complementary to one of the 4-mers in the second array, and each of the 4-mers in any one array having a unique label.

18. A kit according to claim 12, wherein the oligonucleotide probe comprises 64 arrays, each array being comprised of 4 non-spatially separated, labelled 4-mers, wherein each of the 4-mers in any one array is non-complementary to one another and non-overlapping with one another, and each of the 4-mers in any one array is not common to any of the other arrays and has a unique label.

19. The method according to claim 6, wherein fluorescence is measured using a fluorescence microscope.

20. A method according to claim 10, wherein the RNA is contacted with two types of arrays in two separate reactions, wherein each of said two types of arrays is comprised of 128-labelled 4-mers, and further wherein each of the 4-mers in a first type of array being complementary to one another and non-overlapping with one another, and each of the 4-mers in the second type of array being non-complementary to one another and non-overlapping with one another, and wherein each of the 4-mers in said two types of arrays has a unique label.

* * * * *